(12) United States Patent
Takahashi et al.

(10) Patent No.: US 9,274,043 B2
(45) Date of Patent: Mar. 1, 2016

(54) SAMPLE IDENTIFICATION SORTING APPARATUS AND SAMPLE IDENTIFICATION SORTING METHOD

(71) Applicant: Furukawa Electric Co., Ltd., Tokyo (JP)

(72) Inventors: Toru Takahashi, Tokyo (JP); Ken Tsukii, Tokyo (JP); Jie Xu, Tokyo (JP)

(73) Assignee: Furukawa Electric Co., Ltd., Tokyo (JP)

( * ) Notice: Subject to any disclaimer, the term of this patent is extended or adjusted under 35 U.S.C. 154(b) by 0 days.

(21) Appl. No.: 14/638,166

(22) Filed: Mar. 4, 2015

(65) Prior Publication Data

US 2015/0177121 A1    Jun. 25, 2015

Related U.S. Application Data

(63) Continuation of application No. PCT/JP2013/073990, filed on Sep. 5, 2013.

(30) Foreign Application Priority Data

Sep. 6, 2012 (JP) ................................. 2012-196054

(51) Int. Cl.
*G01N 15/14* (2006.01)
*B03B 13/02* (2006.01)

(52) U.S. Cl.
CPC ............ *G01N 15/1459* (2013.01); *B03B 13/02* (2013.01); *G01N 15/14* (2013.01);
(Continued)

(58) Field of Classification Search
CPC .............. G01N 15/14; G01N 15/1459; G01N 15/1404; G01N 2015/149; G01N 2015/1481; G01N 2015/1415; B03B 13/02

USPC ........... 209/577; 73/864.11, 863.11; 356/336; 250/458.1; 422/73
See application file for complete search history.

(56) References Cited

U.S. PATENT DOCUMENTS 5,690,895 A    11/1997  Matsumoto et al.
8,586,890 B2   11/2013  Takahashi et al.
(Continued)

FOREIGN PATENT DOCUMENTS

JP    6-281557 A    10/1994
JP    2009-100698 A    5/2009
(Continued)

OTHER PUBLICATIONS

International Search Report Issued on Oct. 8, 2013 for PCT/JP2013/073990 Filed on Sep. 5, 2013 (English language).
(Continued)

*Primary Examiner* — David H Bollinger
(74) *Attorney, Agent, or Firm* — Oblon, McClelland, Maier & Neustadt, L.L.P.

(57) ABSTRACT

A sample identification sorting apparatus includes an identifying unit having an optical information-measuring section that measures optical information of a sample dispersed in a liquid, and a determining section that determines whether the sample is a target sample or a non-target sample, a sorting unit including a sorting nozzle having a flow path in communication with the flow path of the identifying unit, a liquid waste-collecting section that collects by suction a liquid waste discharged from a sorting nozzle tip, and a container to collect a sorting solution containing a target sample, a moving unit and a control unit that cause the sorting nozzle and/or the collecting container to move relatively based on the optical information. The liquid waste-collecting section has a suction nozzle that sucks a liquid waste containing a non-target sample discharged from the sorting nozzle tip or containing a non-target sample or a non-sortable sample.

11 Claims, 15 Drawing Sheets

(52) U.S. Cl.
CPC ...... *G01N15/1404* (2013.01); *G01N 2015/149* (2013.01); *G01N 2015/1415* (2013.01); *G01N 2015/1481* (2013.01)

(56) References Cited

U.S. PATENT DOCUMENTS

| | | | | |
|---|---|---|---|---|
| 2003/0198523 | A1* | 10/2003 | Bohm | B07C 5/34 406/198 |
| 2003/0234210 | A1* | 12/2003 | Deshpande | B07C 5/02 209/576 |
| 2004/0053243 | A1* | 3/2004 | Evans | A61D 19/00 435/6.19 |
| 2005/0068536 | A1* | 3/2005 | Schwabe | B01L 3/502715 356/436 |
| 2008/0257072 | A1 | 10/2008 | Takahashi et al. | |
| 2009/0107262 | A1 | 4/2009 | Hashimoto et al. | |
| 2010/0007879 | A1 | 1/2010 | Mavliev | |
| 2012/0122084 | A1* | 5/2012 | Wagner | C12N 5/0612 435/6.1 |
| 2012/0153185 | A1 | 6/2012 | Ito et al. | |
| 2014/0309795 | A1* | 10/2014 | Norton | G01N 15/14 700/282 |

FOREIGN PATENT DOCUMENTS

| | | |
|---|---|---|
| JP | 4413921 B2 | 2/2010 |
| JP | 2011-527751 A | 11/2011 |
| JP | 2012-127922 A | 7/2012 |
| WO | WO 2005/103642 A1 | 11/2005 |

OTHER PUBLICATIONS

International Written Opinion Issued on Oct. 8, 2013 for PCT/JP2013/073990 Filed on Sep. 5, 2013.
English translation of the International Preliminary Report on Patentability issued Mar. 19, 2015 in PCT/JP2013/073990.
Written Opinion issued Oct. 8, 2013 in PCT/JP2013/073990 (submitting English translation only, International version previously filed Mar. 4, 2015).

* cited by examiner

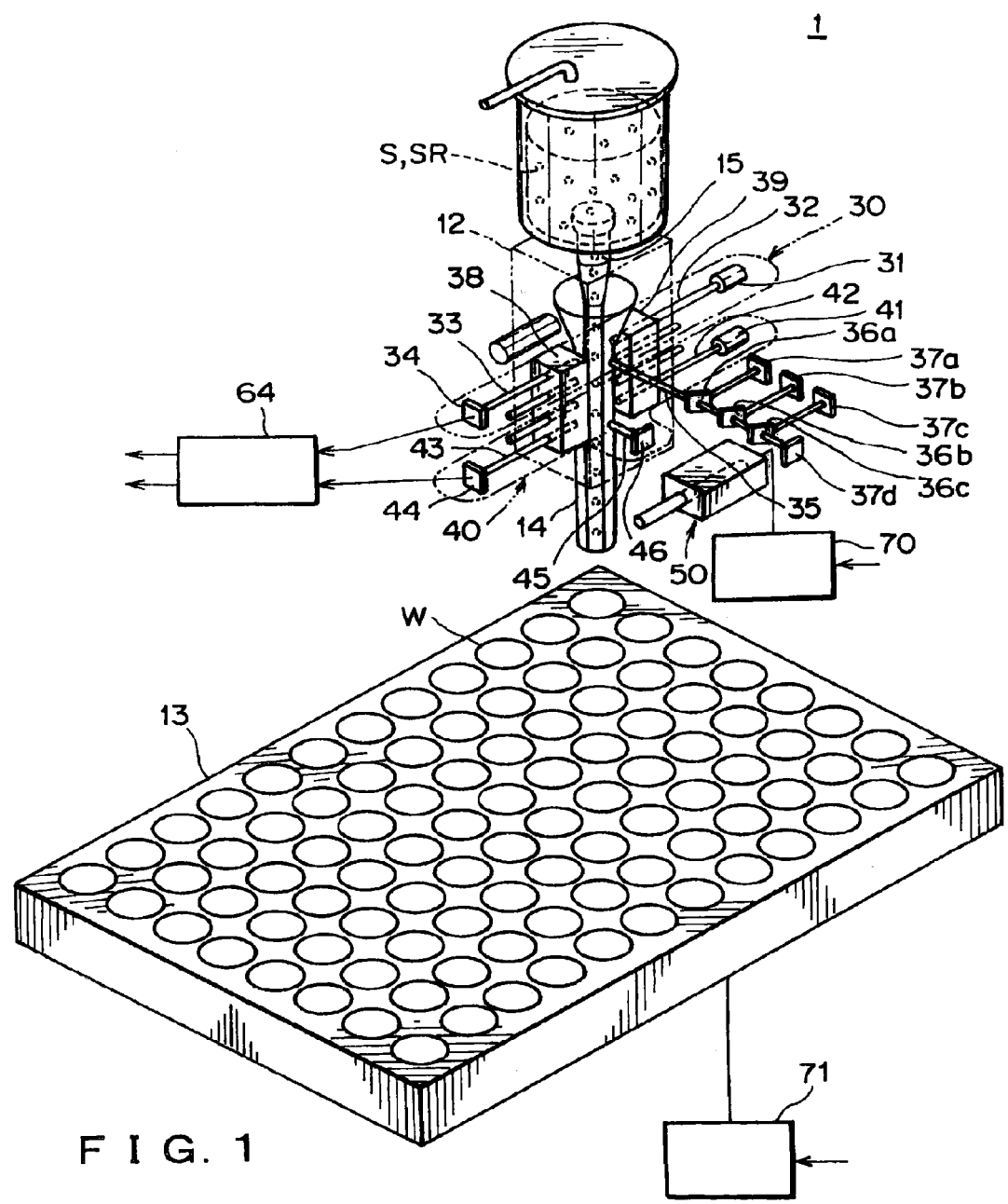
F I G. 1

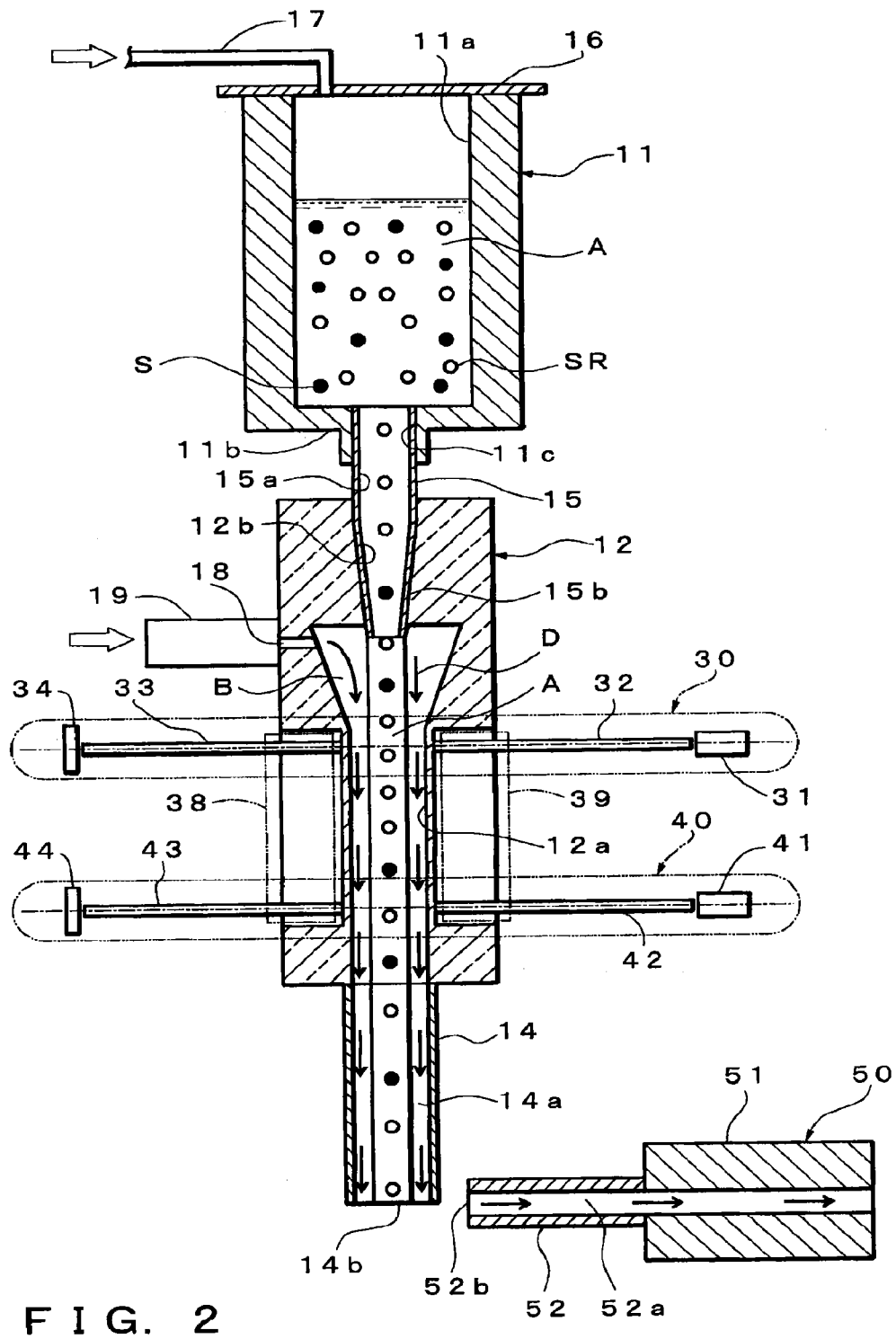
F I G. 2

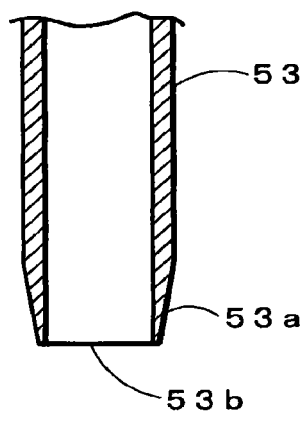 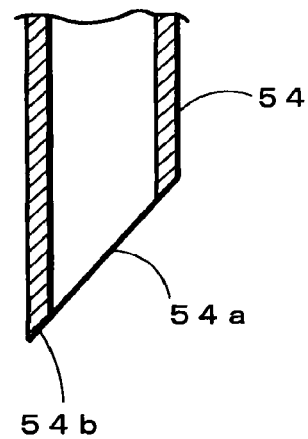
FIG. 6A    FIG. 6B
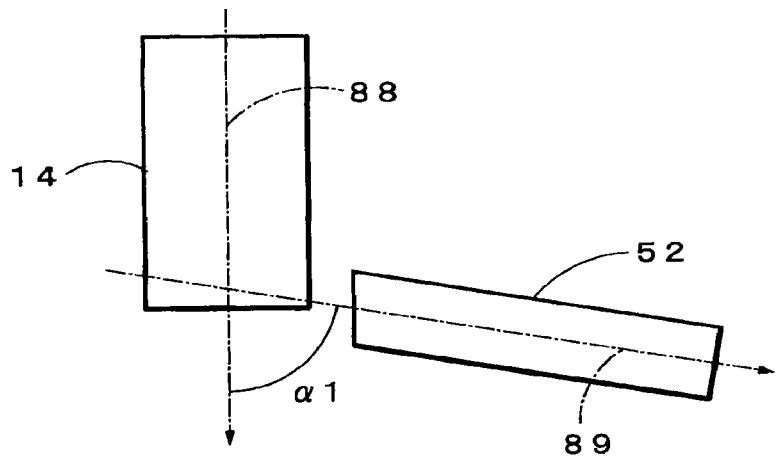
FIG. 8A
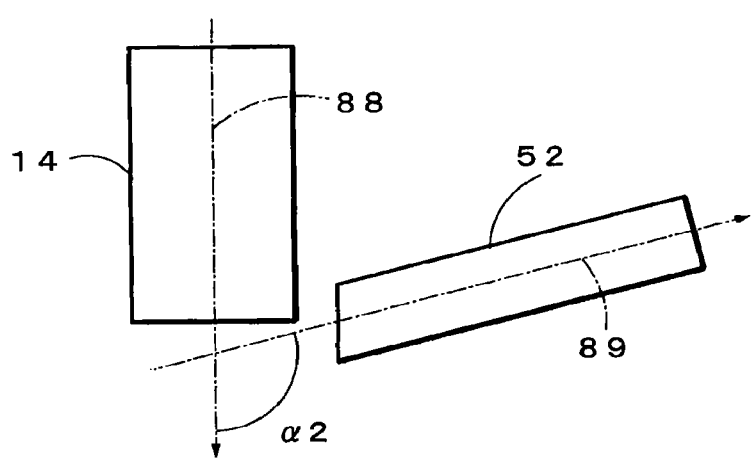
FIG. 8B

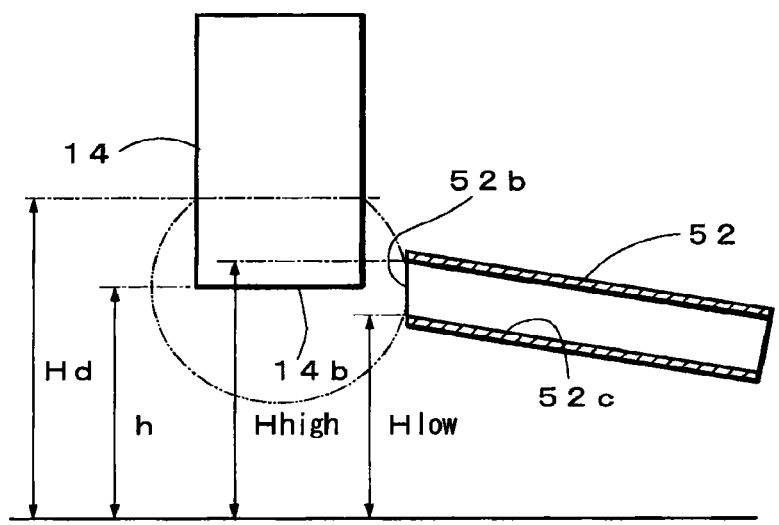
F I G. 9A
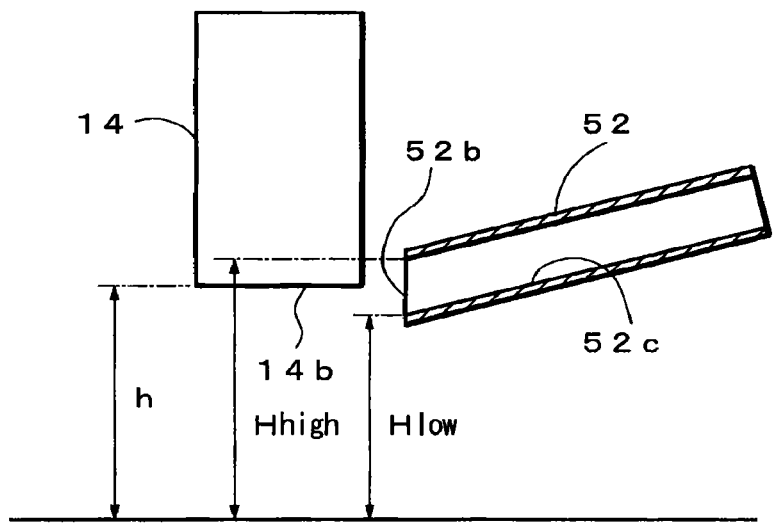
F I G. 9B

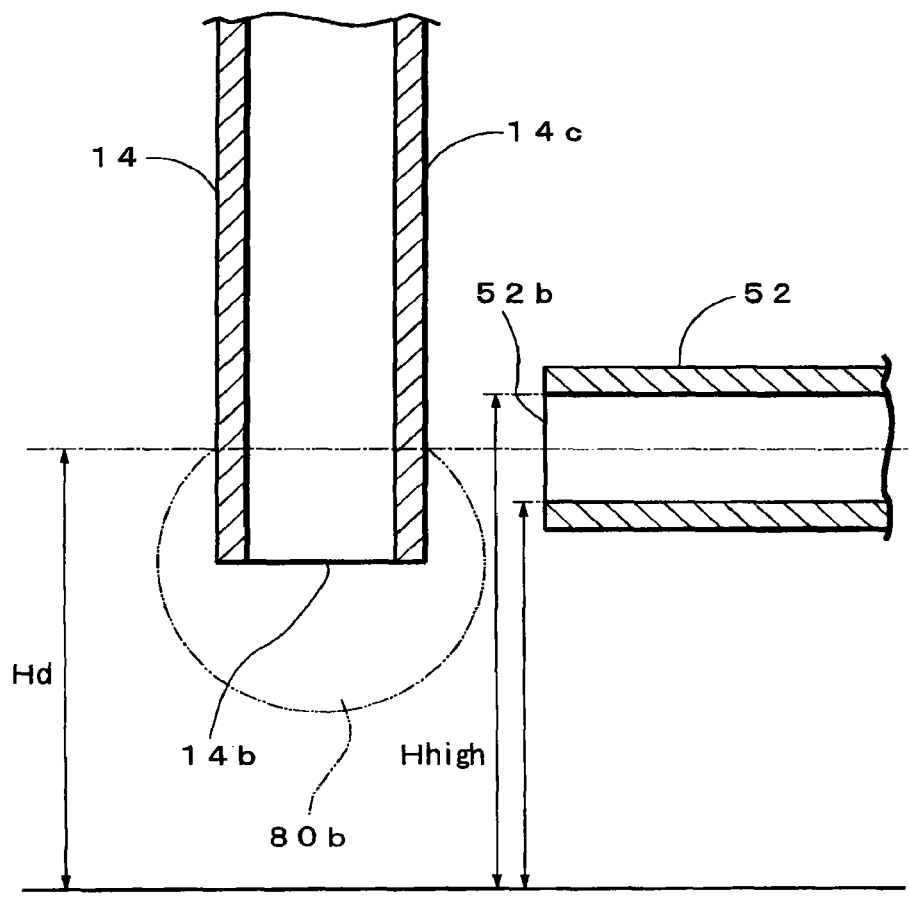
F I G. 1 1
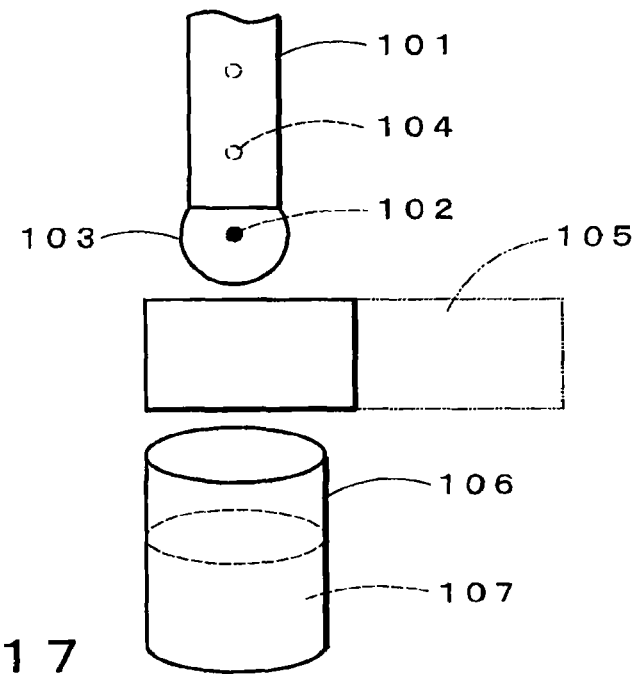
F I G. 1 7

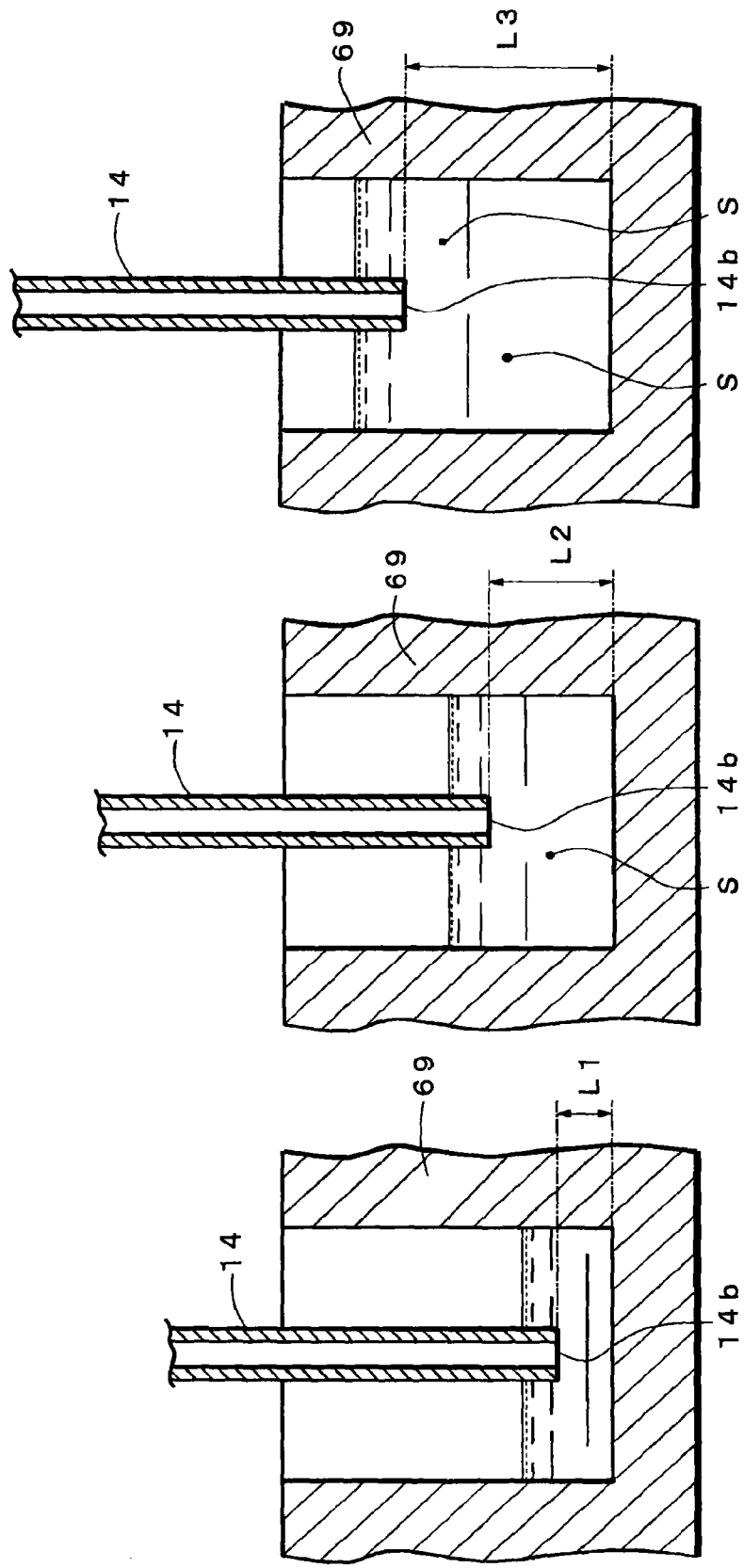

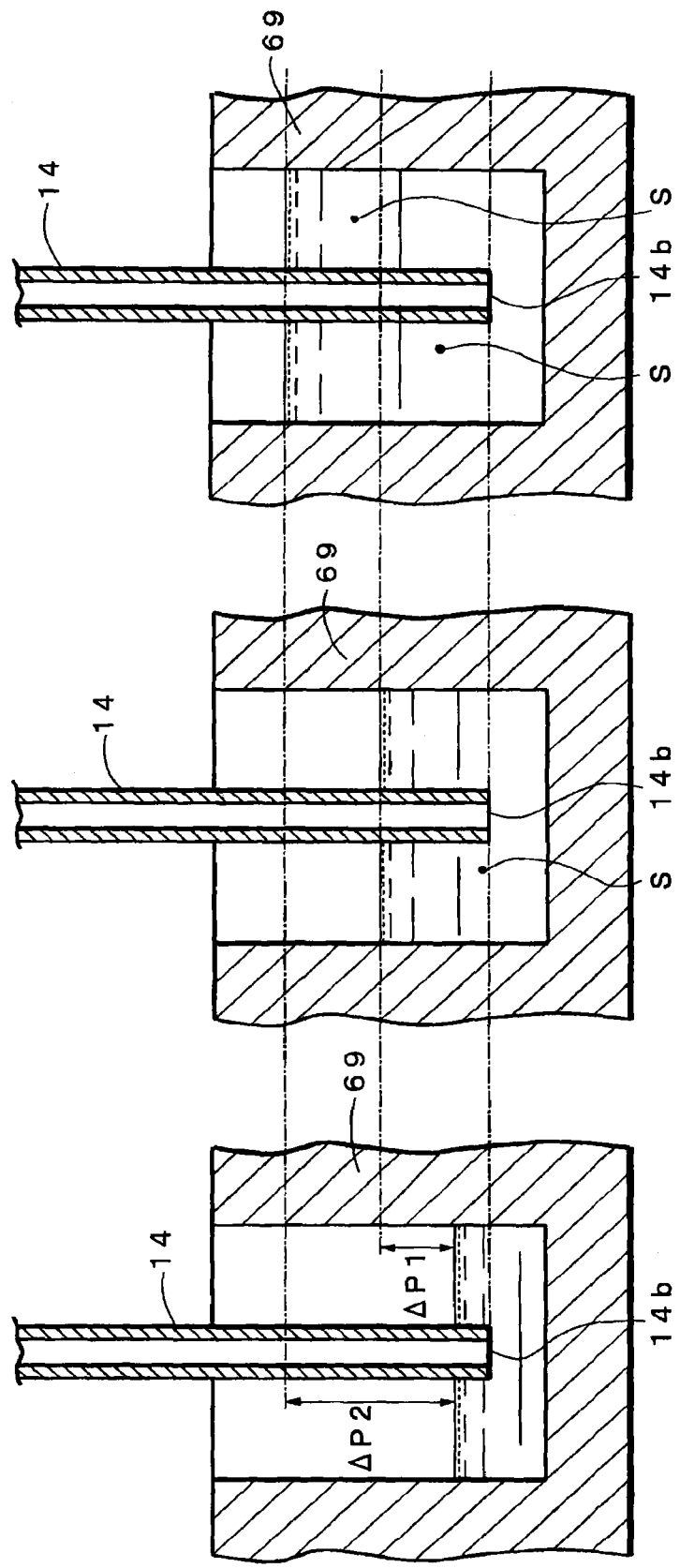

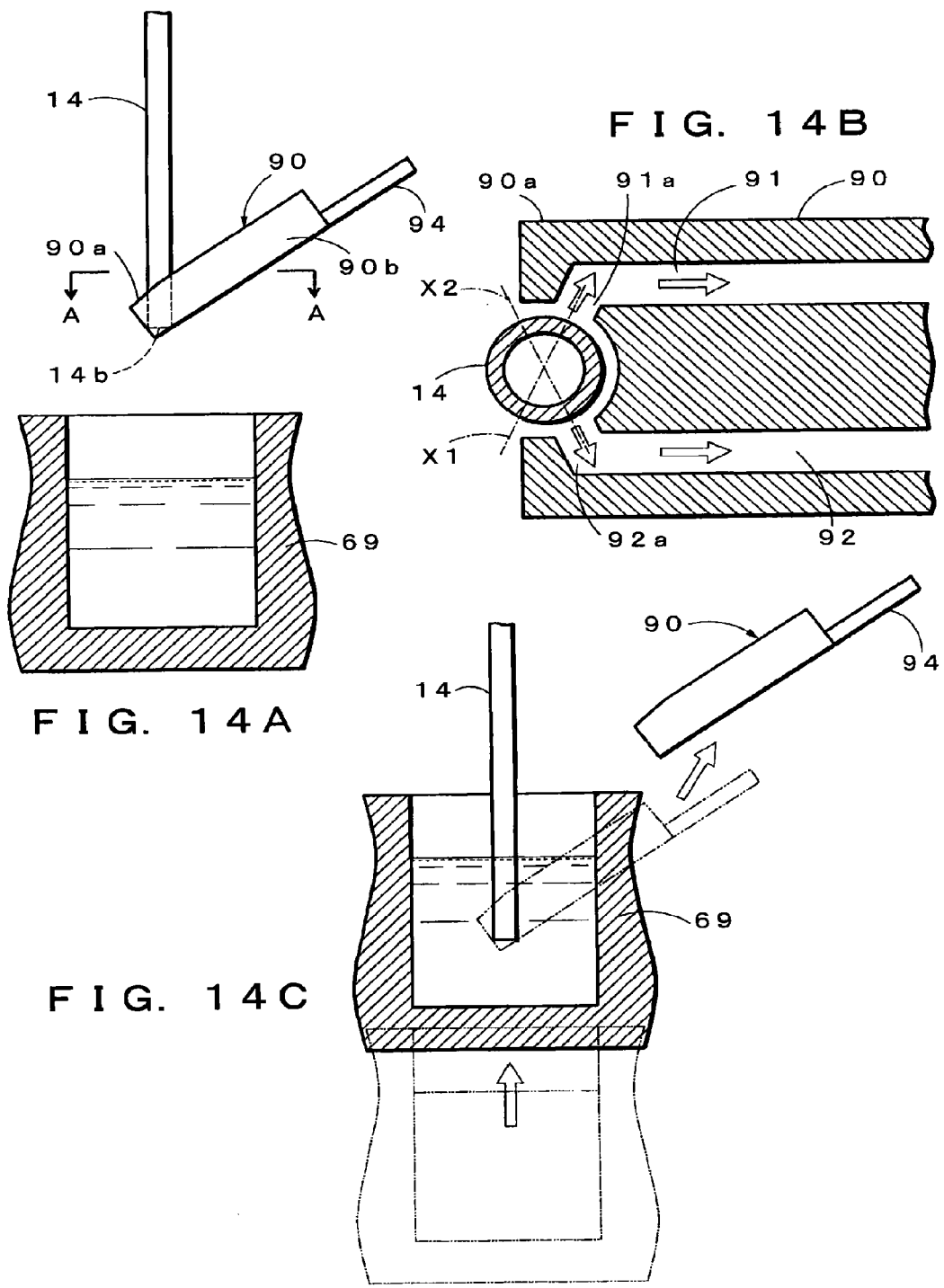

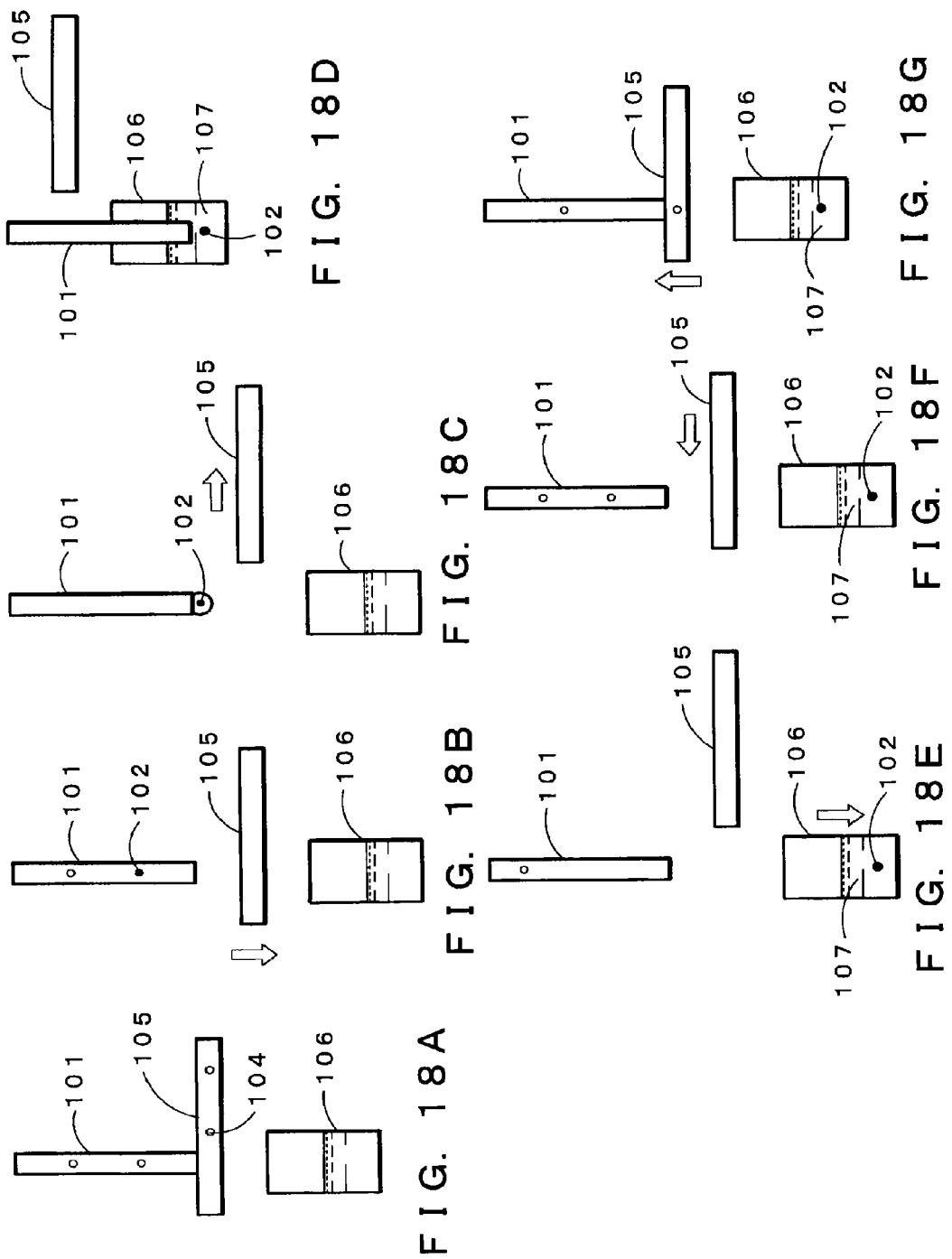

SAMPLE IDENTIFICATION SORTING APPARATUS AND SAMPLE IDENTIFICATION SORTING METHOD

CROSS REFERENCE TO RELATED APPLICATIONS

This is a continuation application of International Patent Application No. PCT/JP2013/073990 filed Sep. 5, 2013, which claims the benefit of Japanese Patent Application No. 2012-196054, filed Sep. 6, 2012, the full contents of all of which are hereby incorporated by reference in their entirety.

BACKGROUND

1. Technical Field

The present disclosure relates to a sample identification sorting apparatus and a sample identification sorting method that identify a sample, which is an object to be measured, dispersed in a liquid and sorts a target sample based on the result of identification.

2. Background

Sample identification sorting apparatuses of the related art are widely used in research and testing in the medical field as an apparatus for identifying and sorting microscopic samples such as cells. Recently, there is a need in research and testing institutions to achieve identification and sorting without sample destruction, and also to increase efficiency in research and testing by accelerating these processes.

In general, a sample identification sorting apparatus comprises a detecting section and a sorting section. The detecting section detects optical information obtained by irradiating light on a single sample. The sorting section collects necessary samples based on the detection result and discards unnecessary samples.

FIG. 17 is a diagram showing an example of the configuration of the sorting section in the sample identification sorting apparatus of the related art, and FIGS. 18A to 18G are diagrams showing an example of an operation of the aforementioned sorting section.

FIG. 17 shows that, in the sorting section, a droplet 103 or a liquid stream is formed at a tip of a sorting nozzle 101 at a predetermined pressure with a target sample 102 being contained therein. When a non-target sample 104 is contained therein, the droplet 103 or liquid stream is discharged into a liquid waste reservoir 105 (FIG. 18A). When a target sample 102 is contained in the droplet 103 or liquid stream, the liquid waste reservoir 105 is withdrawn in a downward direction and further moved in a lateral direction (FIGS. 18B and 18C) and the collecting container 106 is moved in a vertical direction with a moving unit, not shown, and inserted into the collecting container 106 filled with liquid 107 to carry out the sorting of the target samples 102 (FIG. 18D). Thereafter, an operation in reverse order to the aforementioned operation is performed to return the liquid waste reservoir 105 to the position shown in FIG. 18A and the sorting process is finished (FIGS. 18E to 18G). According to this configuration, since sorting can be performed without a droplet being formed using ultrasound or a high voltage and without applying unnecessary load on the samples, for example, in a case where living cells are targets, a high survival rate after the sorting is expected. (E.g., see Japanese Patent No. 4413921).

However, with the aforementioned configuration of the related art, there are problems described below. That is, since target samples are discharged from a tip of the sorting nozzle before entering into the collecting container, there is a problem that the target samples may be damaged or contaminated by coming in contact with an end face and/or an external wall of the tip of the sorting nozzle. Also, a target sample is not always located at the center of a droplet discharged from a tip of the sorting nozzle, and when it is located at an interface between the droplet and air, it may be damaged due to surface tension. Particularly, when the target sample is a living cell or a susceptible living cell, there is a possibility of cell destruction which may lead to a decrease in cell survival rate after sorting and a decrease in working efficiency.

With a configuration in which non-target samples are collected in a liquid waste reservoir, many steps such as a downward movement and a lateral movement of the liquid waste reservoir, an upward movement and a downward movement of the collecting container, and a lateral movement and an upward movement of the liquid waste reservoir are necessary, and it is difficult to seek for a rapid sorting process.

It is an object of the present disclosure to provide a sample identification sorting apparatus and a sample identification sorting method that can prevent samples from being damage or contaminated when sorting target samples and achieving a rapid sorting process.

SUMMARY

According to an aspect of the disclosure, a sample identification sorting apparatus of the present disclosure is a sample identification sorting apparatus that identifies a sample dispersed in a liquid, the sample being an object to be measured, and sorts a target sample based on a result of identification, the sample identification sorting apparatus including an identifying unit having a sample storage section configured to store a sample dispersed in a liquid, a pressure controlling section that delivers the liquid to a flow channel, a light irradiating section that irradiates light on a sample, an optical information measuring section that measures optical information of the sample, and a determining section that determines whether the sample is a target sample or a non-target sample, a sorting unit having a sorting nozzle configured to sort a sorting solution containing a target sample into a collecting container, the sorting nozzle having a flow path in communication with the flow path of the identifying unit, a liquid waste collecting section that is configured to perform collection by suction of one of a liquid waste discharged from a tip of the sorting nozzle and a liquid waste containing a non-target sample or a sample determined as being not possible to be sorted, and a collecting container that is configured to collect a sorting solution containing a target sample, a moving unit that moves at least one of the sorting nozzle and the collecting container, and a control unit that causes at least one of the sorting nozzle and the collecting container to move relative to each other based on the optical information measured in the optical information measuring section, the liquid waste collecting section having a suction nozzle that is configured to suck one of a liquid waste containing a non-target sample discharged from the tip of the sorting nozzle and a liquid waste containing a non-target sample or a sample determined as being not possible to be sorted.

It is preferable that the suction nozzle has a plurality of suction paths. Further, the moving unit moves the suction nozzle. Preferably, the moving unit causes the suction nozzle to come close to the sorting nozzle from a lateral direction thereof.

Preferably, the control unit calculates a flow velocity V of a target sample, and based on the flow velocity V, calculates time T taken for the target sample to arrive at the tip of the sorting nozzle, the control unit being configured to cause at least one of the sorting nozzle and the collecting container to move relative to each other to immerse the tip of the sorting nozzle into a liquid in the collecting container before the time T elapses.

More preferably, when the suction nozzle tip has come close to the sorting nozzle, a lowest end point height h of the tip of the sorting nozzle is lower than a highest point height $H_{high}$ of an inner periphery of the tip of the sorting nozzle.

More preferably, when the suction nozzle tip has come close to the sorting nozzle, the lowest end point height h of the tip of the sorting nozzle is lower than the highest point height $H_{high}$ of the inner periphery of the tip of the sorting nozzle and also lower than a lowest point height $H_{low}$ of the inner periphery of the tip of the sorting nozzle.

Also, it is preferable that the moving unit causes the suction nozzle to come close to the sorting nozzle from the lateral direction thereof such that a flow direction at the suction nozzle tip forms a predetermined angle α with respect to a flow direction at the tip of the sorting nozzle, where the predetermined angle α satisfies:

$$70°<\alpha<110°.$$

Further, it is preferable that, when causing at least one of the sorting nozzle and the collecting container to move relative to each other, the control unit increases a distance between the tip of the sorting nozzle and the collecting container depending on an increase in a number of times of detection of the target sample.

Further, it is preferable that, the delivery pressure in the flow path of the sorting nozzle is changed depending on a signal from the control unit, and the pressure controlling section increases a delivery pressure of the liquid containing the target sample depending on an increase in a number of times of detection of the target sample when causing at least one of the sorting nozzle and the collecting container to move relative to each other.

According to a further aspect of the present disclosure, a sample identification sorting method of identifying a sample dispersed in a liquid, the sample being an object to be measured, and sorts a target sample based on a result of identification is provided, the sample identification sorting method including a storing step of storing a sample dispersed in a liquid, a delivering step of delivering the liquid to a flow path, an irradiating step of irradiating light on the sample, a measuring step of measuring optical information of the sample, a determining step of determining whether the sample is a target sample or a non-target sample based on the optical information, a collecting step of performing, by a suction nozzle, collection by suction of one of a liquid waste discharged from a tip of a sorting nozzle that is in communication with the flow path and a liquid waste containing a non-target sample or a sample determined as being not possible to be sorted, a controlling step of causing, based on the determination result of the determining step, at least one of the sorting nozzle and the collecting container to move relative to each other such that the tip of the sorting nozzle is inserted into the collecting container, and a sorting step of sorting a sorting solution containing the target sample discharged from the tip of the sorting nozzle into the collecting container.

According to the present disclosure, it is determined whether the sample is a target sample or a non-target sample based on the optical information, and, based on the optical information, at least one of the sorting nozzle and the collecting container are caused to move relative to each other such that the tip of the sorting nozzle is inserted into the collecting container. And, a sorting solution containing the target sample discharged from the tip of the sorting nozzle is sorted into the collecting container. Thereby, a target sample is collected into a liquid in the collecting container without coming into contact with an end face or an external wall of the sorting nozzle or air and the target sample can be prevented from being contaminated or damaged. Also, since a liquid waste containing a non-target sample discharged from the tip of the sorting nozzle is collected by suction with a suction nozzle laterally of the sorting nozzle, the distance of travel or the operation time of the mechanical operation of moving the liquid waste collecting section can be shortened and the sorting process can be made faster as compared to the configuration of the related art. Particularly, in the configuration of the related art, since the liquid waste collecting section is disposed below the sorting nozzle, it was necessary to firstly withdraw the liquid waste collecting section from below the sorting nozzle during the sorting. On the other hand, according to the present disclosure, since the liquid waste collecting section is disposed laterally of the sorting nozzle, it is not necessary to withdraw the liquid waste collecting section from below the sorting nozzle during the sorting, and the time required for the entire sorting process can be significantly shortened.

BRIEF DESCRIPTION OF DRAWINGS

FIG. 1 is a perspective diagram schematically showing a configuration of an entirety of a sample identification sorting apparatus according to an embodiment of the present disclosure.

FIG. 2 is a partial cross-sectional view showing, in an enlarged view, a part of the sample identification sorting apparatus of FIG. 1 from a sample storage section to a tip portion of a sorting nozzle.

FIGS. 6A and 6B are diagrams showing a variant of a tip shape of the sorting nozzle.

FIGS. 8A and 8B are diagrams for explaining an angle between a flow direction of the sorting nozzle and a flow direction of the suction nozzle during liquid waste collection.

FIGS. 9A and 9B are diagrams for explaining a positional relationship between the tip of the sorting nozzle and the tip of the suction nozzle during liquid waste collection.

FIG. 11 is a diagram showing another variant of the positional relationship between the tip of the sorting nozzle and the tip of the suction nozzle.

FIGS. 12A to 12C are diagrams for explaining a change in a movement position of the sorting nozzle during the sorting solution collection.

FIGS. 13A to 13C are diagrams for explaining a variant of a sample identification sorting process.

FIG. 14A is a side view showing a variant of the suction nozzle; FIG. 14B is a cross sectional view taken along line A-A of FIG. 14A; and FIG. 14C is a diagram for explaining an operation of the suction nozzle of FIG. 14A.

FIG. 17 is diagram showing an example of a configuration of the sorting section of a sample identification sorting apparatus of the related art.

FIGS. 18A to 18G are diagrams showing an example of the operation of the sorting section of FIG. 17.

DETAILED DESCRIPTION

Figure 3:
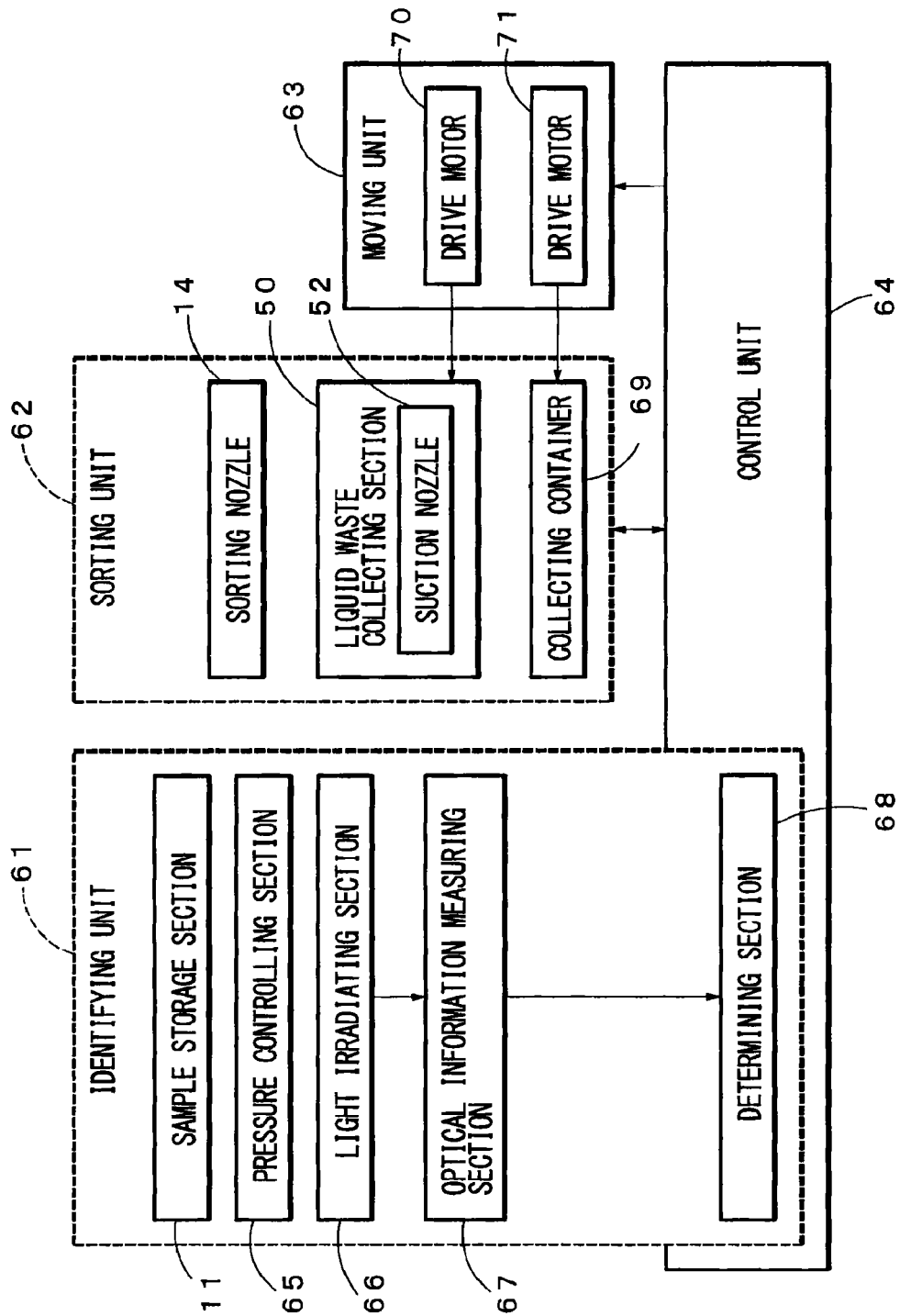
FIG. 3 is a block diagram for explaining functions of the sample identification sorting apparatus of FIG. 1.

Further features of the present disclosure will become apparent from the following detailed description of exemplary embodiments with reference to the accompanying drawings.

FIG. 1 is a perspective diagram schematically showing a configuration of an entirety of a sample identification sorting apparatus according to an embodiment of the present disclosure. The sample identification sorting apparatus is an apparatus that measures optical information of a sample by irradiating excitation light on a sample such as a cell which is an object to be measured dispersed in a liquid flowing through a flow path, and based on the optical information, determines whether it is necessary to sort the sample or not, and sorts the target sample, which was determined to be sorted, into a collecting container.

In FIGS. 1 and 2, samples S indicated by white dots are target samples that are objects to sorted, and samples SR indicated by black dots are non-target samples that are objects to be rejected.

As shown in FIGS. 1 and 2, a sample identification sorting apparatus 1 includes a sample storage section 11 that stores samples S and SR dispersed in a liquid A, a flow cell 12 having a flow path 12a through which the liquid A flows, and a sorting nozzle 14 that has a flow path 14a communicating with the flow path 12a of the flow cell 12 and sorts a sorting solution containing the sample S to a culture plate 13 (collecting container). The liquid A is a sample suspension in which the sample S and the sample SR are dispersed in a solution.

The sample storage section 11 is disposed above the flow cell 12. An introduction nozzle 15 is disposed between the sample storage section 11 and the flow cell 12, and the introduction nozzle 15 has a linear flow path 15a that introduces the liquid A from the sample storage section 11 into the flow path 12a of the flow cell 12. The sorting nozzle 14 having a linear flow path 14a that introduces the liquid A flowing through the flow path 12a thereof into a well of culture plate 13 is disposed below the flow cell 12.

The sample storage section 11 is a cylindrical container having an opening portion 11a at an upper part thereof through which the liquid A is introduced and a discharge port 11c in a base wall 11b thereof. That is, the sample storage section 11 has a function of storing the samples dispersed in the liquid A. Also, a cover 16 that can be opened and closed is placed on the opening portion 11a of the sample storage section 11. The cover 16 is provided with a pipe 17 to introduce a pressurized air adjusted to a predetermined pressure into the sample storage section 11. By introducing the pressurized air into the sample storage section 11 through the pipe 17, the liquid A is delivered to the flow path 15a at the predetermined pressure.

In order to introduces the liquid A into the sample storage section 11, for example, in a state where the sample storage section 11 is arranged in connection with the introduction nozzle 15, the cover 16 is opened and the liquid A is introduced into the sample storage section 11 through the opening portion 11a using a pipette or the like.

The introduction nozzle 15 is a cylindrical member having a predetermined cross-sectional shape, and has a tapered portion 15b at a lower end side. An upper end portion of the introduction nozzle 15 is secured to a base wall 11b of the sample storage section 11 so that an inlet side of the flow path 15a communicates with an discharge port 11c of the sample storage section 11. The tapered portion 15b of the introduction nozzle 15 is secured to the tapered opening 12b formed at an upper end of the flow cell 12 and in communication with the flow path 12a by press fitting or threading. Note that, instead of the tapered portion 15b and the tapered opening 12b, a linear portion or an opening without a taper may be formed.

The flow cell 12 is provided with a sheath liquid introduction opening 18 which is in communication with the linear flow path 12a and through which a liquid (sheath liquid) B is introduced into the flow path 12a, which liquid B being a liquid that does not contain any sample. The flow cell 12 is provided with a sheath liquid introducing section 19 that introduces, into the sheath liquid introduction opening 18, the sheath liquid B regulated to a predetermined pressure.

In the flow path 12a of the flow cell 12, the liquid A is surrounded by the sheath liquid B so that the samples S and SR dispersed in the liquid A flow individually. A stream of liquid A is referred to as a sample stream and a stream of the sheath liquid B in a shape surrounding the sample stream is referred to as a sheath stream.

The sorting nozzle 14 is secured to a lower end portion of the flow cell 12 in such a manner that the flow path 12a of the flow cell 12 and the linear shaped flow path 14a of the sorting nozzle 14 are in communication with each other. The flow cell 12 and the sorting nozzle 14 may be provided as separate bodies or may be configured as an integrated body.

As described above, the linear flow path 15a of the introduction nozzle 15 is in communication with the discharge port 11c of the sample storage section 11, and the linear flow path 12a of the flow cell 12 is in communication with the flow path 15a, and further the linear flow path 14a of the sorting nozzle 14 is in communication with the flow path 12a. Accordingly, a flow path from the sample storage section 11 to the tip portion of the sorting nozzle 14 form a flow path having a linear shape.

Further, the sample identification sorting apparatus 1 is provided with measurement systems 30 and 40 that irradiate excitation light on the sample S and SR contained in the liquid A flowing through the flow path 12a in the flow cell 12, and measure optical information of the samples. As shown in FIGS. 1 and 2, the measurement system 30, 40 are two measurement systems which are disposed around the flow path 12a at two different positions with respect to a direction of travel of the samples S and SR contained in the liquid A flowing through the flow path 12a in the flow cell 12 (flow direction D in the flow path of the sample stream). With each measurement system 30, 40, excitation light is irradiated individually on the samples at different positions in the direction of travel of the samples, and optical information of the sample is measured.

The measurement system 30 is provided with a light irradiating section that irradiates excitation light on a sample flowing through the flow path 12a of the flow cell 12, a transmitted light receiver that receives transmitted light which is the excitation light that has penetrated through the sample, and a side scattered light receiver that receives side scattered light and fluorescence from the sample.

The light irradiating section of the measurement system 30 is provided with a semiconductor laser element 31 that emits laser light (e.g., light of 488 nm) of a predetermined wavelength as excitation light and an irradiation optical fiber 32 that propagates the laser light and emits it in the vicinity of a stream (sample stream) of the liquid A flowing through the flow path 12a.

The transmitted light receiver of the measurement system 30 includes an optical fiber 33 that receives the transmitted light from the sample in the vicinity of sample stream and a light receiving element 34 that receives the transmitted light which has propagated through the optical fiber 33.

The side scattered light receiving section of the measurement system 30 is provided with an optical fiber 35 that receives the side scattered light from the sample in the vicinity of the sample stream, three optical filters 36a to 36c that are provided in the optical fiber 35 and separates the side scattered light and fluorescence contained therein for each wavelength, and four light receiving elements 37a to 37d that receive light separated by each optical filter.

The light receiving element 37a receives the side scattered light reflected on the optical filter 36a. The light receiving element 37b receives the fluorescence that has penetrated through the optical filter 36a and reflected on the optical filter 36b. The light receiving element 37c receives the fluorescence that has penetrated through the optical filter 36b and reflected on the optical filter 36c. The light receiving element 37d receives the fluorescence that has penetrated through the optical filter 36c.

The measurement system 40 is provided with a light irradiating section that irradiates a sample flowing through the flow path 12a in the flow cell 12 with excitation light, a transmitted light receiver that receives the transmitted light which is the excitation light that has penetrated through the sample, and a fluorescence receiver that receives the fluorescence from the sample.

The light irradiating section of measurement system 40 is provided with a semiconductor laser element 41 that emits laser light (e.g., light of 635 nm) of a predetermined wavelength as excitation light and an irradiation optical fiber 42 that propagates the laser light and emits it in the vicinity of the sample stream. In the present embodiment, a semiconductor laser element is employed as a light source, but it may be a light source that emits light of a specific wavelength.

The transmitted light receiver of the measurement system 40 includes an optical fiber 43 that receives the transmitted light from the sample in the vicinity of the sample stream, and a light receiving element 44 that receives the transmitted light that has propagated through the optical fiber 43.

Each of the optical fibers 32, 33, 35, 42 and 43 of the measurement systems 30 and 40 is held by optical fiber holding members 38, 39 and is positioned and secured by the optical fiber hold members 38, 39 with respect to the flow cell 12. Positions of the optical fiber hold members 38, 39 are optionally adjustable with respect to the stream of samples.

The fluorescence receiver of the measurement system 40 is provided with an optical fiber 45 that receives the fluorescence from the sample in the vicinity of the sample stream and a light receiving element 46 that receives the fluorescence that has propagated through the optical fiber 45.

Further, the sample identification sorting apparatus 1 is configured to determine whether the sample is a target sample or a non-target sample, and based on the determination result, moves the culture plate 13 before the target sample arrives at the tip 14b of the sorting nozzle 14 to sort the sorting solution containing the target sample into a well W of the culture plate 13. Specifically, the sample identification sorting apparatus 1 is provided with a stage, not shown, that supports the culture plate 13 so as to be movable with respect to the sorting nozzle 14, and a drive motor that drives this stage, which will be described below.

The sample identification sorting apparatus 1 is provided with a liquid waste collecting section 50 that collects a liquid waste containing a non-target sample discharged from the tip 14b of the sorting nozzle 14. The liquid waste collecting section 50 includes a liquid waste collecting section main body 51 and a suction nozzle 52 that extends laterally from a side surface of the liquid waste collecting section main body 51 and sucks, through a flow path 52a, the liquid waste containing the non-target sample discharged from the tip of the sorting nozzle (FIG. 2). Further, the sample identification sorting apparatus 1 has a stage, not shown, that supports the suction nozzle 52 so as to be movable with respect to the sorting nozzle 14, and a drive motor described below that drives this stage. Here, the liquid waste or the sorting solution refers to the liquid A, the sheath liquid B or a liquid which is a mixture thereof and discharged to an outside from the end face 14b of the sorting nozzle 14.

FIG. 3 is a block diagram for explaining functions of the sample identification sorting apparatus of FIG. 1.

In FIG. 3, the sample identification sorting apparatus 1 is provided with an identifying unit 61, a sorting unit 62, a moving unit 63 and a control unit 64.

The identifying unit 61 includes the sample storage section 11 that stores samples dispersed in a liquid, a pressure controlling section 65 for delivering a liquid to the flow path, a light irradiating section 66 for irradiating light on a sample, an optical information measuring section 67 that measures optical information of the sample, and a determining section 68 that determines, based on the optical information, whether the sample is a target sample or a non-target sample. The optical information measuring section 67 is a function block corresponding to the measurement systems 30 and 40 of FIG. 1.

The sorting unit 62 includes the sorting nozzle 14 that has a flow path in communication with the flow path of the identifying unit 61 and sorting the sorting solution containing the target sample into the collecting container described below, a liquid waste collecting section 50 that perform collection by suction of the liquid waste containing the non-target sample discharged from the tip of the sorting nozzle, and a collecting container 69 that collects the sorting solution containing the target sample. Note that the collecting container 69 corresponds to the culture plate 13 of the aforementioned embodiment.

The moving unit 63 has a drive motor 70 that drives the liquid waste collecting section 50 and a drive motor 71 that drives the collecting container 69, and the drive motors 70 and 71 move the liquid waste collecting section 50 and the collecting container 69 via a stage, not shown.

The control unit 64 determines whether the sample is a target sample (sample S) or a non-target sample (sample SR) based on optical information (each information of transmitted light, side scattered light and fluorescence) obtained at each light receiving section, i.e., each of the light receiving elements 34, 44, 37a to 37d and 46, of the measurement systems 30 and 40. Further, the control unit 64 is capable of measuring a flow velocity V of the sample S, SR from a difference in time of measurement of optical information obtained by each light receiving element 34 and 44 of the measurement system 30 and 40 and an interval between the light receiving element 34, 44, and also capable of calculating time T taken for the sample S, SR to arrive at the tip portion of the sorting nozzle 14 based on the measured flow velocity V. Note that, in the present embodiment, a part of the control unit 64 constitutes the determining section 68, but the control unit 64 and the determining section 68 may be provided separately.

Then, in a case where it is determined that the sample is a sample S, the drive control of the drive motor 71 is carried out before the calculated time T elapses. Thereby, the collecting container 69 moves in an upward direction, and the tip 14b of the sorting nozzle 14 is inserted into the liquid in the collecting container 69, and thereafter, the sorting solution 50 containing the sample S in the tip 14b is sorted into a liquid in the collecting container 69. That is, the control unit 64 calculates the flow velocity V of the sample S based on the optical information measured by the optical information measuring section 67, and calculates time T for the sample S to arrive at the tip 14b of the sorting nozzle 14 based on the flow velocity V. Then, the control unit 64 moves the collecting container 69 so that the tip 14b of the sorting nozzle 14 is immersed in the liquid in the collecting container before the time T elapses.

FIGS. 4A to 4D are diagrams for explaining an operation of the sorting unit 62 in FIG. 3, and FIGS. 5A to 5D are enlarged views in the vicinity of the sorting nozzle during the operation shown in FIGS. 4A to 4D.

Figure 4A:
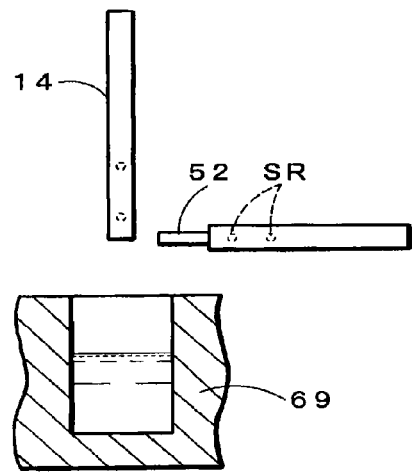
FIGS. 4A to 4D are diagrams for explaining an operation of a sorting unit of FIG. 3.
Figure 5A:
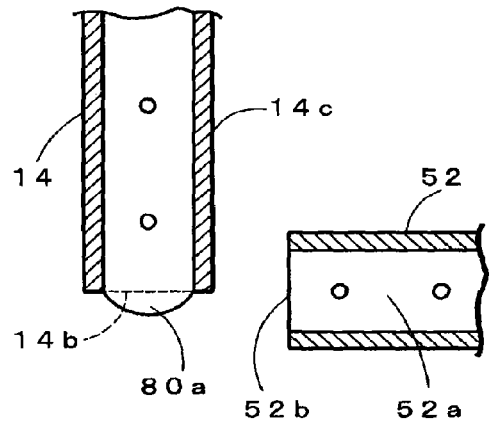
FIGS. 5A to 5D are enlarged views in the vicinity of the sorting nozzle during the operation shown in FIGS. 4A to 4D.
Figure 5B:
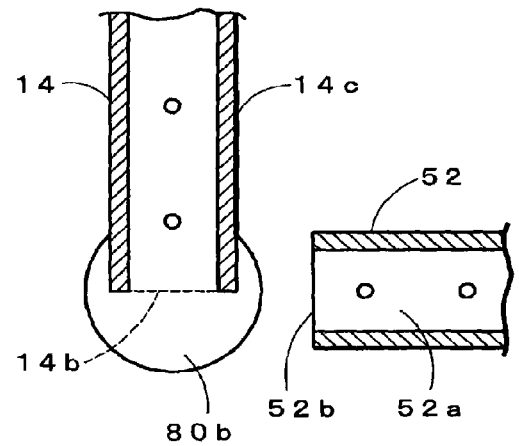
Figure 5C:
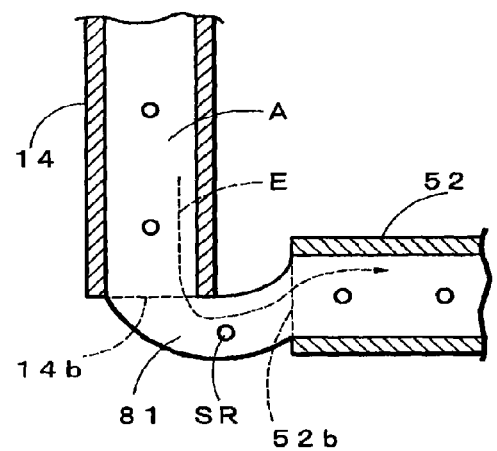

First, in a stand-by state, the suction nozzle 52 is at rest at a proximate position, which is from a position at which the suction nozzle 52 is not in contact with the sorting nozzle 14 and about 1 mm from the side surface 14c of the sorting nozzle 14, and sucks a liquid waste discharged from the tip of the sorting nozzle or a liquid waste containing the non-target sample SR and/or the target sample S which is determined as being not possible to be sorted (FIG. 4A). At this time, the liquid waste is discharged with a predetermined pressure from the tip 14b of the sorting nozzle 14, and becomes a liquid waste 80a having a downwardly convex shape (FIG. 5A), and it is further drawn upwards along an outer wall 14c by an action of surface tension of the sorting nozzle 14, and becomes a liquid waste 80b having a substantially spherical shape (FIG. 5B). Then, the liquid waste 80b becomes a liquid waste 81 flowing from the tip 14b to the tip 52b by a suction force of the suction nozzle 52 (arrow E in FIG. 5C). At this time, it is preferable that a surface of the tip 52b of the suction nozzle is provided substantially in parallel with a flow direction in the sorting nozzle 14. Thus, the liquid waste can be sucked positively.

Figure 4B:
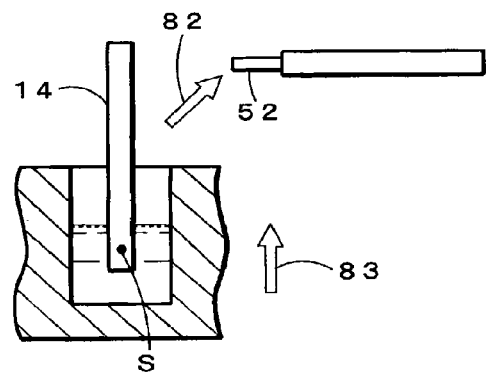
Figure 4C:
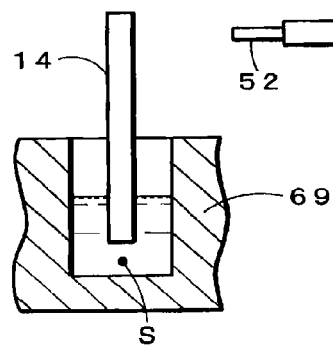
Figure 5D:
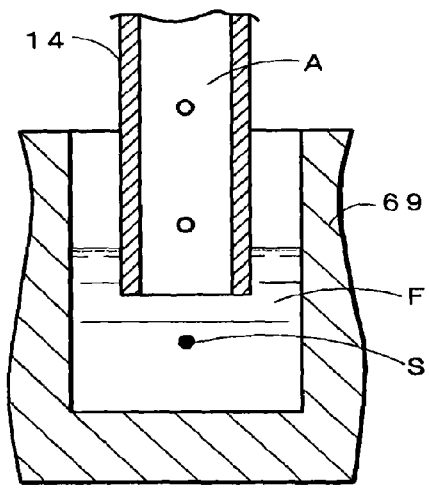

In a case where the sample is determined to be a sample S that can be sorted, the suction nozzle 52 is moved in an upward direction by driving the drive motor 70 at a predetermined timing (arrow 82) (FIG. 4B). This operation of the suction nozzle 52 is performed by a single operation of moving in an obliquely upward direction or in a vertically upward direction. Also, simultaneously with an upward movement of the suction nozzle 52, the collecting container 69 moves in an upward direction by the drive motor 71 (arrow 83), and the collecting container 69 stops at a position where the tip 14b of the sorting nozzle 14 is inserted into the liquid in the collecting container 69. That is, the sorting nozzle 14 is inserted into the collecting container 69 before the sample S is discharged from the sorting nozzle 14. Time required from the beginning of the movement of the suction nozzle 52 to the insertion of the sorting nozzle 14 into the liquid in the collecting container 69 is, for example, 40 ms. Also, time T taken for the sample S to be discharged from the tip of the sorting nozzle 14 is, for example, 70 ms. Thereafter, the sorting solution 86 containing the sample S is sorted into the collecting container 69 (FIG. 4C). At this time, the sorting solution 86 containing the sample S is mixed with liquid F in the collecting container 69 without coming in contact with air and the end surface of the tip 14b (FIG. 5D).

Figure 4D:
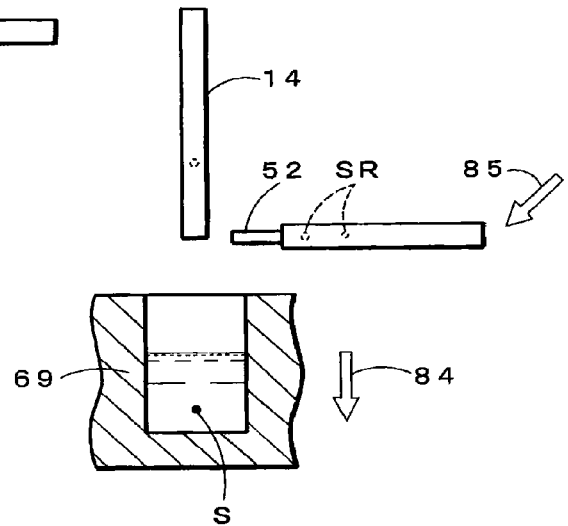

When the sample S is sorted, the collecting container 69 moves in a downward direction by the drive motor 71 (arrow 84) (FIG. 4D). Further, simultaneously with a movement in downward direction of the collecting container 69 or after the movement has started, the suction nozzle 52 moves in a downward direction by the drive motor 70 (arrow 85). This operation of the suction nozzle 52 is performed by a single operation of moving in an obliquely downward direction or a vertically downward direction. The time required from the beginning of the movement of the collecting container 69 to the stoppage of the suction nozzle 52 is, for example, 120 ms. With this operation, the suction nozzle 52 and the collecting container 69 returns to standby positions, and the suction nozzle 52 sucks again the liquid waste containing the sample SR discharged from the tip 14b of the sorting nozzle 14.

Note that, during the movement of the collecting container 69 in a downward direction, there may be a case where the liquid F in the collecting container 69 attaches to an outer wall 14c and or the tip 14b of the sorting nozzle 14, and a part of the attached liquid F hangs down to the collecting container 69 and may cause contamination of the target sample S. Also, with a droplet containing the target sample S being attached to the sorting nozzle 14, there may be case where the target sample S is not sorted into the collecting container 69 and this may result in a decrease in sorting accuracy. Thus, the sorting nozzle 53 having a tapered portion 53a at an end portion may be employed as a variant of the sorting nozzle 14 (FIG. 6A). Thereby, the draining of the water attached to the tapered portion 53a and the end 53b improves, and it becomes possible to suppress contamination of the target sample S due to the hanging down of the liquid. Also, the sorting nozzle 54 having a cut surface 54a having an end that is cut at a predetermined angle with respect to the flow direction may be employed (FIG. 6B). This shape also provides an improved draining of the liquid attached to the tapered portion 54a and the end 54b.

Figure 7:
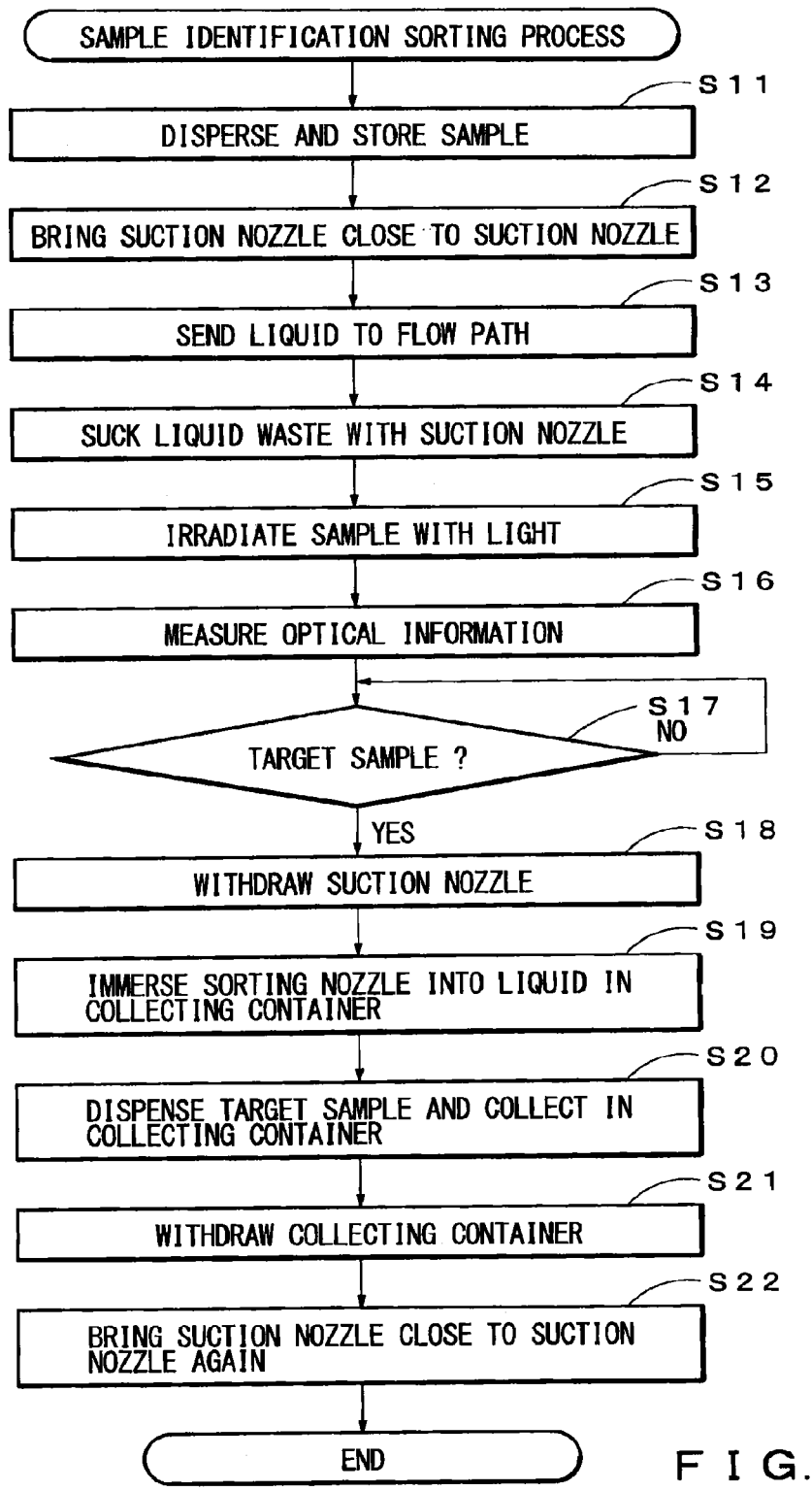
FIG. 7 is a flow chart of a sample identification sorting process performed in the sample identification sorting apparatus of FIG. 1.

FIG. 7 is a flow chart of a sample identification sorting process performed in the sample identification sorting apparatus of FIG. 1.

At first, the samples S, SR dispersed in the liquid A are stored in the sample storage section 11 (step S11), and the tip 52b of the suction nozzle 52 is caused to come close to the tip 14b of the sorting nozzle 14 and stopped at the standby position (step S12). Then, a predetermined pressure is added from the pipe 17, and the liquid A is delivered to the flow path 14a (step S13).

Then, excitation light is irradiated on the samples S, SR flowing through the flow path 14a (step S15), the optical information received at each light receiving element is measured (step S16), and, based on this optical information, it is determined whether each sample flowing through the flow path 14a is a sample S which is a target sample or sample SR which is a non-target sample (step S17).

In a case where each sample flowing through the flow path 14a is a sample S which is a target sample, the suction nozzle 52 is withdrawn from the standby position and the tip 52b of the suction nozzle 52 is separated away from the tip 14b of the sorting nozzle 14 (step S18). Also, together with the withdrawal of the suction nozzle 52, the collecting container 69 is moved and the tip 14b of the sorting nozzle 14 is immersed into the liquid in the collecting container 69 (step S19). Then, the sorting solution containing the sample S is sorted into the collecting container 69 and the sample S is collected in the collecting container 69 (step S20). Thereafter, the collecting container 69 is moved and withdrawn to the standby position (step S21) and the suction nozzle 52 is moved again to the standby position and the tip 52b of the suction nozzle 52 is caused to come close to the tip 14b of the sorting nozzle 14 (step S22), and this process is terminated.

As mentioned above, according to the present embodiment, the flow velocity V of the target sample is calculated based on optical information of the sample S, and time T taken for the sample S to arrive at the tip of the sorting nozzle is calculated based on the flow velocity V. Also, the collecting container 69 is moved so that the tip of the sorting nozzle is immersed into the liquid in the collecting container 69 before time T elapses. Thereafter, the sorting solution 86 containing the sample S discharged from the tip 14b of the sorting nozzle 14 is sorted into the collecting container 69. Thereby, the sample S is collected into the liquid in the collecting container 69 without coming into contact with an end portion and an external wall of the sorting nozzle 14 or air, and damages and contaminations caused by the sample S coming into contact with the sorting nozzle 14 and air can be prevented. Also, since the liquid waste containing the sample SR discharged from the tip 14b of the sorting nozzle 14 is sucked and collected, the distance of travel or the operation time of the mechanical operation of moving the liquid waste collecting section in an upward direction or a downward direction can be significantly shortened and the sorting process can be made faster as compared to the configuration of the related art.

Here, since the suction nozzle 52 performs suction with a pressure sufficient to suck the liquid waste from the sorting nozzle 14, this suction pressure may affect the liquid A and the sheath liquid B flowing through the flow path 14a of the sorting nozzle 14. That is, the suction force may give acceleration to the stream of sample in the vicinity of the tip 14b and may change the flow velocity V, and there is a possibility that the sample S is discharged from the sorting nozzle 14 at a timing earlier than the time T calculated by the control unit 64. Also, when a position of the suction nozzle 52 to the sorting nozzle 14 is inappropriate, the liquid waste from the sorting nozzle 14 cannot be sucked effectively.

Thus, at first, in the present embodiment, an angle between the flow direction of the sorting nozzle 14 and the flow direction of the suction nozzle 52 at the time of the liquid waste collection is set as follows. That is, as shown in FIGS. 8A and 8B, the moving unit 63 causes the suction nozzle 52 to come close to the sorting nozzle 14 in a lateral direction thereof in such a manner that a flow direction 89 at the tip 52b of the suction nozzle 52 forms a predetermined angle α with a flow direction 88 at the tip 14b of the sorting nozzle 14. Preferably, a predetermined angle α1 is set so as to be greater than 70° and less than 180° (FIG. 8A), and preferably, a predetermined angle α2 is set so as to be greater than 70° and less than 110° (FIG. 8B). Thereby, an effect of the suction force of the suction nozzle 52 on the liquid A and the sheath liquid B flowing through the flow path 14a of the sorting nozzle 14 can be significantly suppressed and an accurate sorting process can be performed. Furthermore, in a case where the predetermined angle α is greater than 80° and less than 90°, the effect of the suction force of the suction nozzle 52 on the liquid A and the sheath liquid B flowing through the flow path 14a of the sorting nozzle 14 can be suppressed and also dropping of the liquid waste from the vicinity of the tip 52b of the suction nozzle 52 can be suppressed.

Also, the sucking effect by the suction nozzle 52 can be restrained by a positional relationship between the tip 14b of the sorting nozzle 14 and the tip 52b of the suction nozzle 52 during the liquid waste collection. In practice, since a droplet which is formed at the tip 14b of the sorting nozzle 14 is somewhat drawn upward along an outer wall 14c due to surface tension as shown in FIG. 5B, it is preferable to determine the positional relationship between the tip 14b of the sorting nozzle 14 and the tip 52b of the suction nozzle 52 by taking in consideration the amount drawn upward of the droplet.

FIGS. 9A and 9B are diagrams for explaining a specific positional relationship between the tip 14b of the sorting nozzle 14 and the tip 52b of the suction nozzle 52 at the time of the liquid waste collection. Note that FIGS. 9A and 9B are diagrams corresponding to FIGS. 8A and 8B, and illustrate cases where α1=80° and α2=100°, respectively.

When the suction nozzle 52 has come close to the sorting nozzle 14, a lowest end point height h of the tip 14b of the sorting nozzle 14 is higher than a lowest point height $H_{low}$ of an inner periphery at the tip 52b of the suction nozzle 52 and lower than a highest point height $H_{high}$ of the inner periphery, and further $H_{low}$ is set to be lower than Hd. Here, the lowest point height of the inner periphery is defined as a height of the lowest point of an inner surface 52c of the suction nozzle and the highest point height of the inner periphery is defined as a height of the highest point of the inner surface 52c of the suction nozzle. Further, Hd is defined as a height of an upper end portion of a spherical droplet formed at the tip 14b of the sorting nozzle 14. With such positional relationship, since the sorting nozzle sucks a part of the droplet which is drawn upward laterally of the sorting nozzle by surface tension, disturbance due to the suction force of the suction nozzle 52 on the sample stream is mitigated by a side wall of the sorting nozzle 14. Thus, an effect on the liquid A and the sheath liquid B flowing through the flow path 14a can be further suppressed, and a more accurate sorting process can be performed.

The cases where α1=80° and α2=100° were taken as examples and described above with reference to FIGS. 9A and 9B, but as long as the lowest end point height h of a of the tip 14b of the sorting nozzle 14 satisfies the relationships of $h<H_{high}$ and $H_{low}<Hd$, the predetermined angle α may be set to any value.

Figure 10A:
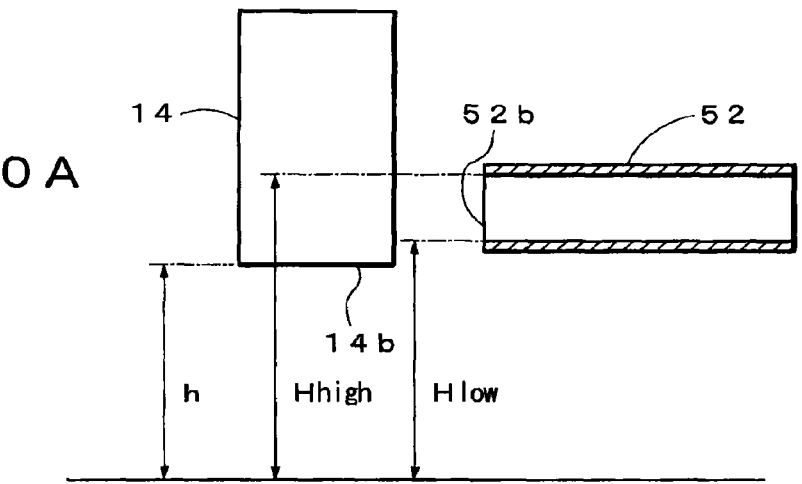
FIGS. 10A to 10D are a side view and horizontal cross sectional views, respectively, showing a variant of the positional relationship between the tip of the sorting nozzle and the tip of the suction nozzle.
Figure 10B:
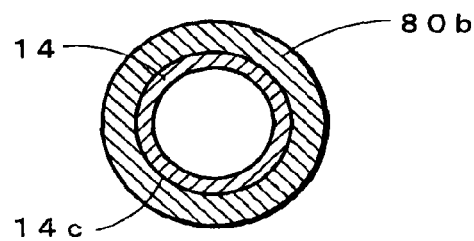
Figure 10C:
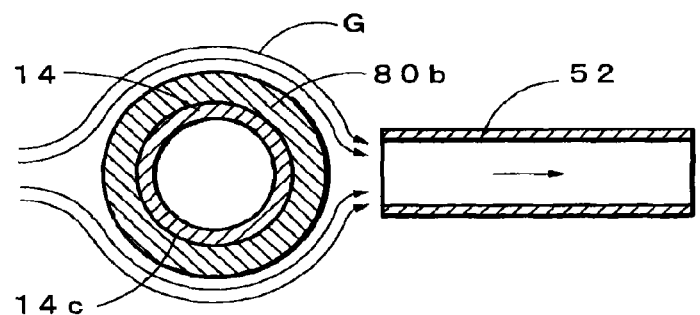
Figure 10D:
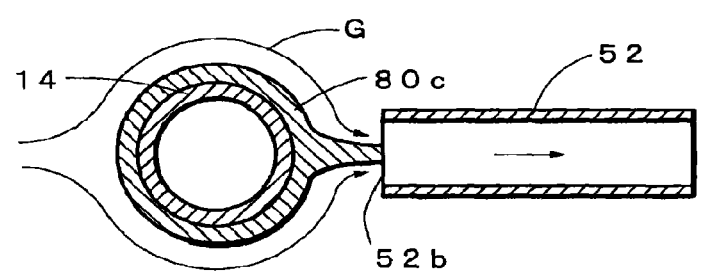

Also, the lowest end point height h of the tip 14b of the sorting nozzle 14 may be set lower than the lowest point height $H_{low}$ of the inner periphery at the tip 52b of the suction nozzle 52 (FIG. 10A). In a case where $h<H_{low}$, air in the vicinity of the droplet 80b which is drawn upward along the outer wall 14c of the sorting nozzle 14 (FIG. 10B) is sucked into the suction nozzle 52, and thus an air flow G around a circular cylinder is formed around a nozzle (FIG. 10C). Due to an action of this air flow G, the droplet 80b is sucked near the central of the suction nozzle 52 together with air. Thereby, almost all of the droplet that is drawn upward laterally of the nozzle is sucked. With such positional relationship, the droplet remaining on the outer wall 14c of the sorting nozzle and which may contain a non-target sample SR or a target sample S that has been determined as being not possible to be sorted will almost be eliminated. Therefore, the liquid waste can be sucked without affecting the sample stream, and, in addition, the liquid waste can be sucked in such a manner that the droplet around the sorting nozzle 14 does not remain. As a result, an accurate sorting process can be performed.

Further, regarding the condition of $H_{low}<Hd$, as shown in FIG. 11, it is more preferable that the center position of the suction nozzle 52 is disposed at the same height as the height Hd of the upper end portion of the droplet 80b or around such height. By performing a suction operation at this positional relationship, a more accurate sorting process can be performed.

Then, in the sorting process, in a case where the sorting nozzle 14 is immersed in the same well W of the collecting container 69 several times, an amount of solution in the collecting container 69 will not always be constant, and will increase depending on a number of times of sorting. Therefore, in a case where a positional relationship between the sorting nozzle 14 in the sorting and the collecting container 69 is constant, the pressure at the tip 14b of the sorting nozzle 14 will vary depending on a water pressure of the solution in the collecting container 69, and this water pressure may affect the liquid A and the sheath liquid B flowing through the flow path 14a of the sorting nozzle 14.

Thus, in the present embodiment, the control unit 64 is configured to store the number of times the sample S was detected in step S16 of FIG. 7, and, a movement position of the collecting container 69 can be changed in accordance with the number of times of detection of the sample S.

Specifically, in a first sorting process, the collecting container is moved in such a manner that a distance between the tip 14b of the sorting nozzle 14 and a bottom surface of the well W in the collecting container 69 is L1 (FIG. 12A). In a second sorting process, the collecting container is moved in such a manner that the distance between the tip 14b of the sorting nozzle 14 and the bottom surface of the well W in the collecting container 69 is L2 (L1<L2) (FIG. 12B). Further, in the third sorting process, the collecting container is moved in such a manner that the distance between the tip 14b of the sorting nozzle 14 and the bottom surface of the well W in the collecting container 69 is L3 (L2<L3) (FIG. 12C). That is, depending on an increase in the number of times of detection of the sample S, the distance between the tip 14b of the sorting nozzle 14 and the collecting container is increased. Thereby, even if an amount of solution in the collecting container 69 increases in accordance with the number of times of detection of the sample S, the distance between the tip 14b of the sorting nozzle 14 and the water surface becomes constant and thus the water pressure in the tip 14b of the sorting nozzle 14 can be made approximately constant, and an accurate sorting process can be performed. Note that, as another control method, a distance from a water surface to 14b may be defined as L, and a control to make the distance L constant may be performed by the moving unit 63.

Also, in a case where the positional relationship between sorting nozzle 14 and the collecting container 69 is constant during sorting, a delivering pressure at the tip 14b of the sorting nozzle 14 can be varied. In this case, the pressure controlling section 65 is configured to change the delivering pressure at the tip 14b of the sorting nozzle 14 in accordance with a signal from the control unit 64. The control unit 64 increases the delivering pressure of the liquid containing the sample S in accordance with an increase in the number of times of detection of the sample S when causing the collecting container 69 to move. The amount of change of the delivering pressure may be constant, or may increase or decrease depending on the number of times of detection.

For example, as shown in FIGS. 13A to 13C, in a case where the first sorting process is performed with a positional relationship as shown in FIG. 13A, pressure controlling for adding Δ P1 corresponding to the depth of the tip 14b of the sorting nozzle 14 to a normal control pressure P is performed in the second sorting process (FIG. 13B). Similarly, in the third sorting process, pressure controlling for adding Δ P2 corresponding to the depth of the tip 14b of the sorting nozzle 14 to control pressure P is performed (FIG. 13C).

According to this configuration, even in a case where water pressure at the tip 14b of the sorting nozzle 14 has increased due to an increase in the amount of solution in the collecting container 69, an accurate sorting process can be performed by dispensing the liquid from the tip 14b of the sorting nozzle 14 at a delivering pressure corresponding to the relevant water pressure.

Note that, in the embodiment, the liquid waste collecting section 50 having the suction nozzle 52 is provided, but as long as it is a configuration in which steps S19 and S20 of sorting process of the present disclosure are performed, the suction nozzle is not necessarily required. Instead of the liquid waste collecting section 50, a liquid waste reservoir configured to collect a liquid waste or a liquid waste containing a non-target sample SR or target sample S determined as being not possible to be sorted discharged from the tip of the sorting nozzle may be provided. This liquid waste reservoir may be the one similar to that of the conventional configuration and can also achieve the aforementioned effect by this configuration.

Also, in the sorting process, the collecting container 69 is moved while securing the sorting nozzle 14, but it is not limited thereto, and the drive motor, not shown, that drives the sorting nozzle 14 may be provided, and the sorting nozzle 14 may be moved and the collecting container 69 may be secured. Also, both the sorting nozzle 14 and the collecting container 69 may be moved relative to each other.

Also, in the embodiment, a single suction nozzle is provided with a single suction path, but it is not limited thereto, and a single suction nozzle may be provided with two or more suction paths.

For example, as shown in FIGS. 14A and 14B, a suction nozzle 90 may be configured as an integrated component provided with two suction openings 91 and 92 having center axes X1 and X2, respectively, in mutually different directions, and opening portions 91a and 92a at one end being disposed proximate to each other. Preferably, in a plan view, an angle formed between the central axes X1 and X2 is greater than 0° and less than 180°. Pipes or the like, not shown, for sucking the liquid waste by a negative pressure are connected to another end sides of the suction opening 91 and 92. When sucking the liquid waste, the opening portions 91a and 92a of the suction nozzle 90 is moved to be in proximity with the vicinity of the tip 14b of the sorting nozzle 14, and the liquid waste discharged from the sorting nozzle 14 is sucked from two directions through the suction openings 91 and 92. Also, when dispensing, the suction nozzle 90 is moved obliquely upward and withdrawn and the collecting container is moved upwardly (FIG. 14C).

According to the present configuration, sucking accuracy of the liquid waste can be improved in comparison to a case where sucking is performed with a single suction nozzle. Also, in the case of a single suction nozzle, a dead space is produced at a position opposite a position where a tip of the suction nozzle 90 is disposed with reference to the sorting nozzle 14, and, the liquid waste may remain in this dead space and produce an unevenness in suction. On the other hand, if suction is performed with the two suction openings 91 and 92 being disposed at the aforementioned angle, production of the dead space can be prevented. Thus, the unevenness in suction can be prevented and sorting accuracy can be improved.

Figure 15:
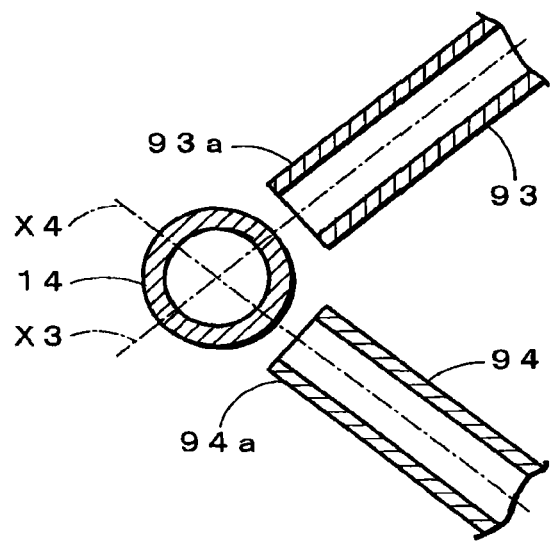
FIG. 15 is a cross sectional view showing a variant of the suction nozzle of FIG. 14B.

Note that the suction nozzle 90 of FIGS. 14A to 14C is provided with two suction openings 91 and 92, but it is not limited thereto, and as shown in FIG. 15, two suction tubes 93 and 94 having central axes X3 and X4, respectively, in mutually different directions, and tips 93a and 94a close to each other may be provided. Thus, an effect similar to the aforementioned effect can be also achieve by a configuration in which two suction paths are provided in separate bodies.

Figure 16:
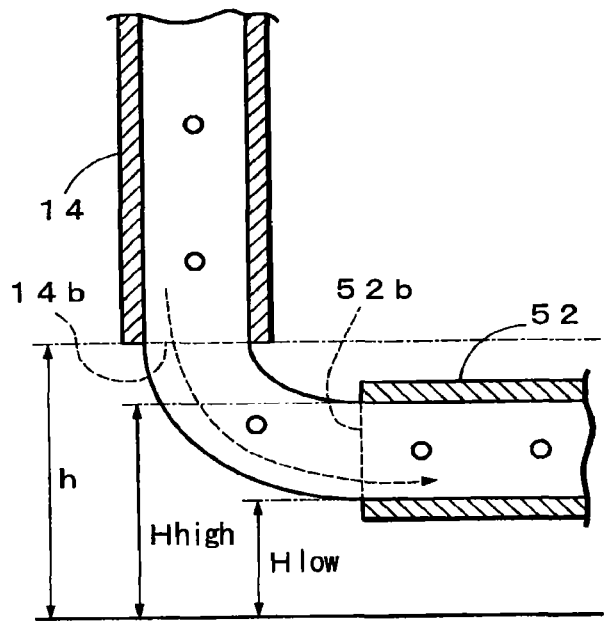
FIG. 16 is a diagram showing a variant of the positional relationship between the tip of the sorting nozzle and the tip of the suction nozzle during liquid waste collection.

Also, in the aforementioned embodiment, the lowest end point height h of the tip 14b of the sorting nozzle 14 is higher than the lowest point height $H_{low}$ of the inner periphery at the tip 52b of the suction nozzle 52 and lower than the highest point height $H_{high}$ of the inner periphery (FIGS. 9A and 9B) or the lowest end point height h of the tip 14b of the sorting nozzle 14 is lower than the lowest point height $H_{low}$ of the inner periphery at the tip 52b of the suction nozzle 52 (FIG. 10A), but it is not limited thereto. As shown in FIG. 16, the lowest end point height h of a of the tip 14b of the sorting nozzle 14 may be set to be higher than the lowest point height $H_{low}$ of the inner periphery at the tip 52b of the suction nozzle 52 and higher than the highest point height $H_{high}$ of the inner periphery.

While certain embodiments have been discussed above for purposes of specifically illustrating the invention contrived by the inventors, it should be understood that the invention is not to be limited to the illustrative embodiments set forth herein and various modifications may be made without departing from the scope and spirit of the invention.

What is claimed is:

1. A sample identification sorting apparatus that identifies a sample dispersed in a liquid, the sample being an object to be measured, and sorts a target sample based on a result of identification, the sample identification sorting apparatus comprising:
   an identifying unit having a sample storage section configured to store a sample dispersed in a liquid, a pressure controlling section that delivers the liquid to a flow channel, a light irradiating section that irradiates light on a sample, an optical information measuring section that measures optical information of the sample, and a determining section that determines whether the sample is a target sample or a non-target sample;
   a sorting unit having a sorting nozzle configured to sort a sorting solution containing a target sample into a collecting container, the sorting nozzle having a flow path in communication with the flow path of the identifying unit, a liquid waste collecting section that is configured to perform collection by suction of one of a liquid waste discharged from a tip of the sorting nozzle and a liquid waste containing a non-target sample or a sample determined as being not possible to be sorted, and a collecting container that is configured to collect a sorting solution containing a target sample;
   a moving unit that moves at least one of the sorting nozzle and the collecting container; and
   a control unit that causes at least one of the sorting nozzle and the collecting container to move relative to each other based on the optical information measured in the optical information measuring section,
   the liquid waste collecting section having a suction nozzle that is configured to suck one of a liquid waste containing a non-target sample discharged from the tip of the sorting nozzle and a liquid waste containing a non-target sample or a sample determined as being not possible to be sorted.

2. The sample identification sorting apparatus according to claim 1, wherein the suction nozzle has a plurality of suction paths.

3. The sample identification sorting apparatus according to claim 1, wherein the moving unit moves the suction nozzle.

4. The sample identification sorting apparatus according to claim 3, wherein the moving unit causes the suction nozzle to come close to the sorting nozzle from a lateral direction thereof.

5. The sample identification sorting apparatus according to claim 4, wherein, the moving unit causes the suction nozzle to come close to the sorting nozzle from the lateral direction thereof such that a flow direction at the suction nozzle tip forms a predetermined angle α with respect to a flow direction at the tip of the sorting nozzle, where the predetermined angle α satisfies:

$$70° < \alpha < 110°.$$

6. The sample identification sorting apparatus according to claim 1, wherein the control unit calculates a flow velocity V of a target sample, and based on the flow velocity V, calculates time T taken for the target sample to arrive at the tip of the sorting nozzle, the control unit being configured to cause at least one of the sorting nozzle and the collecting container to move relative to each other to immerse the tip of the sorting nozzle into a liquid in the collecting container before the time T elapses.

7. The sample identification sorting apparatus according to claim 1, wherein, when the suction nozzle tip has come close to the sorting nozzle, a lowest end point height h of the tip of the sorting nozzle is lower than a highest point height $H_{high}$ of an inner periphery of the tip of the sorting nozzle.

8. The sample identification sorting apparatus according to claim 7, wherein, when the suction nozzle tip has come close to the sorting nozzle, the lowest end point height h of the tip of the sorting nozzle is lower than the highest point height $H_{high}$ of the inner periphery of the tip of the sorting nozzle and also lower than a lowest point height $H_{low}$ of the inner periphery of the tip of the sorting nozzle.

9. The sample identification sorting apparatus according to claim 1, wherein, when causing at least one of the sorting nozzle and the collecting container to move relative to each other, the control unit increases a distance between the tip of the sorting nozzle and the collecting container depending on an increase in a number of times of sorting of the target sample.

10. The sample identification sorting apparatus according to claim 1, wherein the pressure controlling section increases a delivery pressure of the liquid containing the target sample depending on an increase in a number of times of sorting of the target sample when causing at least one of the sorting nozzle and the collecting container to move relative to each other.

11. A sample identification sorting method of identifying a sample dispersed in a liquid, the sample being an object to be measured, and sorts a target sample based on a result of identification, the sample identification sorting method comprising:
   a storing step of storing a sample dispersed in a liquid;
   a delivering step of delivering the liquid to a flow path;
   an irradiating step of irradiating light on the sample;
   a measuring step of measuring optical information of the sample;
   a determining step of determining whether the sample is a target sample or a non-target sample based on the optical information;
   a collecting step of performing, by a suction nozzle, collection by suction of one of a liquid waste discharged from a tip of a sorting nozzle that is in communication with the flow path and a liquid waste containing a non-target sample or a sample determined as being not possible to be sorted;
   a controlling step of causing, based on the optical information, at least one of the sorting nozzle and the collecting container to move relative to each other such that the tip of the sorting nozzle is inserted into the collecting container; and a sorting step of sorting a sorting solution containing the target sample discharged from the tip of the sorting nozzle into the collecting container.

\* \* \* \* \*